Figure 1:
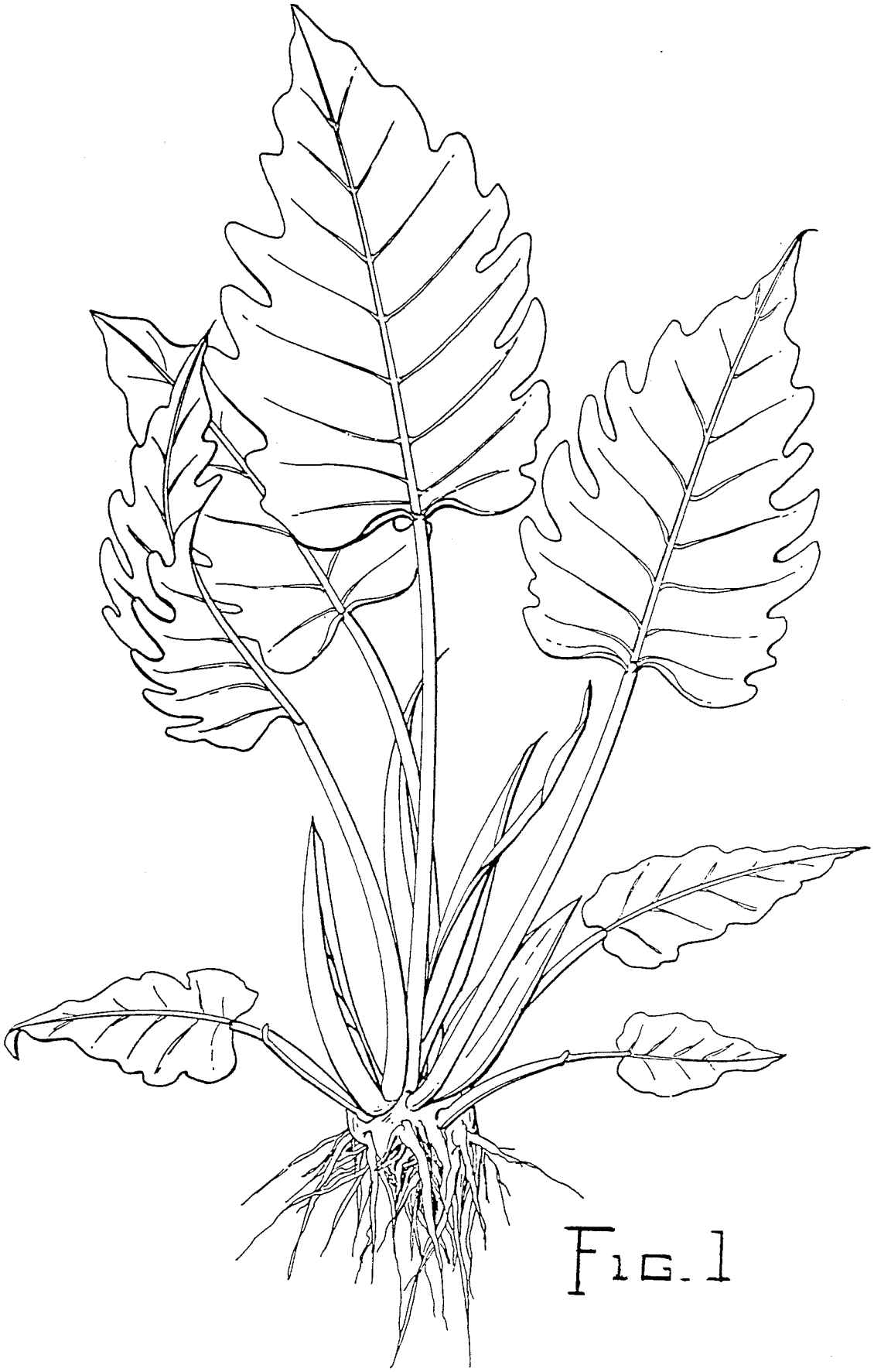

United States Patent [19]

Miller

[11] Patent Number: Plant 6,293

[45] Date of Patent: Sep. 13, 1988

[54] PHILODENDRON PLANT

[75] Inventor: Howard N. Miller, Gainesville, Fla.

[73] Assignee: Cora McColley, Orlando, Fla.

[21] Appl. No.: 918,710

[22] Filed: Oct. 14, 1986

[51] Int. Cl.[4] ..... A01H 5/00

[52] U.S. Cl. ..... Plt./88

[58] Field of Search ..... Plt./88

*Primary Examiner*—Robert E. Bagwill

*Attorney, Agent, or Firm*—Frank B. Robb

[57] ABSTRACT

A self-heading Philodendron plant having uniquely shaped leaves with pronounced lobes that are distinctly hooked. New leaves are moderate reddish brown. Overall color of the plant is reddish to rich-green with reddish brown colored petioles.

2 Drawing Sheets

BACKGROUND AND DESCRIPTION OF THE INVENTION

The present invention comprises a new and distinct cultivar of Philodendron plant which is the result of selecting a seedling from crosses of *Philodendron wendlandii* and *Philodendron bipinnatifidum*, and in turn crossing this selection with a seedling from a cross between *Philodendron wendlandii* and *Philodendron imbe*. From this cross, a single seedling was selected for propagation and is the embodiment of this invention.

An extensive program of Philodendron hybridization has been carried on in the vicinity of Orlando, Fla. and is being continued. Much of the effort is directed toward developing tough, leathery, Philodendron which are compact, self-heading, excellent growers and keepers under in-house environments.

With the increasing emphasis on interior landscaping, there is great demand for new types of Philodendron with distinctive color, form and growth habit. The on-going breeding program has these objectives as a goal. The Philodendron of the instant invention is a compact self-heading plant of distinctive form, leaf type and color which approaches many of the above objectives. I have chosen to call it "Red Empress" for commercial identification.

I have caused the new variety to be asexually reproduced from crown off-shoots. Since the plant is compact, self-heading, and essentially has no stem, ordinary vegetative propagation is not commercially feasible. The plant can be mass produced by tissue culturing. The plant has been found to retain its distinctive characteristics through successive asexual reproduction.

My new variety has been exposed to various conditions in several locations, it has maintained its form and color under a wide range of light, temperature and moisture and thus is considered to be a good indoor foliage plant.

The new plant is distinctive from other Philodendrons in cultivation and is not described by Graf, Bailey or Das Pflanzenreich. The variety to which it may be most nearly compared is a philodendron, unpatented, and sold in the trade as "Venus or Pluto". This plant was also developed by me. It has a similar form but is totally green. There are differences which are noted hereinafter and make the new variety distinctive.

The new variety is visually distinguished by the following characteristics of the leaf, including an ovate form with truncate base and acuminate tip. The margin of the leaf is deeply lobed. The lobes are distinctly hooked toward the apex.

The leaves have pinnate venation with smooth prominent midribs. The width of the leaf is approximately one half the length.

The petioles are erect, round with flat upper surface and are roughly three-fourths the length of the leaves. The leaves are slightly horizontal to erect. The internodes are one-half inch or less.

Since my new variety is without a stem, all petioles appear to be coming from the crown, this aspect being seen in FIG. 1 of the drawing.

The most distinctive aspect of the new variety is its growth habit, the hooked, lobed leaves, the red coloration and the mahogany-colored petioles.

This plant will withstand low light and low soil moisture for weeks. Actually, a low soil moisture content is desirable for maintaining a healthy plant in an indoor environment. Low humidity and temperature fluctuations are not particularly troublesome to maintaining this plant under most conditions. The leaves are of good substance and withstand bruising and dehydration without wilting. Light intensity is not critical. The red coloration is enhanced by moderate light.

My new variety is moderately resistant to bacterial leaf rot, resistant to fungal leaf spots and does not appear to be affected by the physiological problem referred to in the trades as "shot gun" fungus.

This plant is compact with upright symmetrical growth. When three to four plants are placed in a large container an excellent specimen is provided. Under ideal conditions growth is moderate to fast, however the plant does not become leggy or need staking. The average height of year-old plants is 18" to 24" with approximately equal width. An advantage of this plant is that at an early age, liner or four inch pot size, it shows the reddish color of new leaves and the over-all reddish to dark green of mature plants. Growth of microcuttings and young plants is rapid. The growth of the plants indoors is excellent because it is a good specimen plant, tolerates adverse conditions and retains its desired form, size and color longer than many philodendron known to be currently available.

Since the instant variety shares some of the characteristics of prior philodendron varieties and specifically those unpatented varieties mentioned earlier, specific reference thereto is omitted and the details of the instant variety are emphasized in the following detailed specifications, based on observations made in the vicinity of Orlando, Fla.

Figure 2:
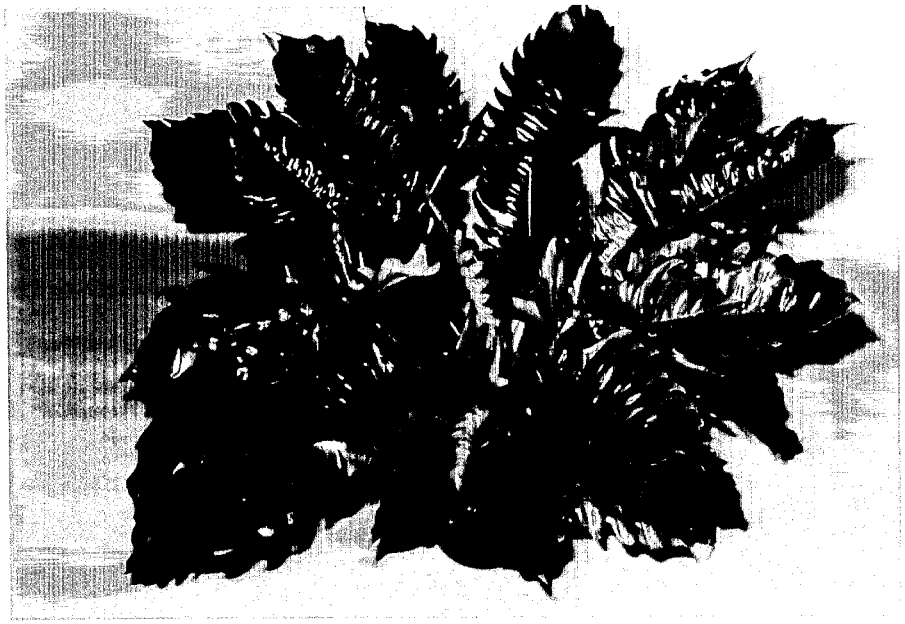

The accompanying drawings, forming a part of this disclosure, shows a typical plant of the new variety in black and white in FIG. 1 and in color in FIG. 2, with the colors being as nearly true as possible in illustrating the variety hereof made by photographic means.

Color references are made to the Munsell Color Cascade published by MacBeth Division of Kollmorgen Company, with observations being recorded by daylight illumination under vinyl of not more than 30% shade.

FORM CHARACTERISTICS

1. Leaf shape:
   a. *Mature.*—Narrowly ovate.
   b. *Immature.*—Narrowly ovate.
   c. *Tip.*—Acuminate.
   d. *Base.*—(1) Mature: Truncate. (2) Immature: Truncate.
   e. *Displacement.*—Undulate.
   f. *Margin.*—Lobed — lobes hooked toward tip.
   g. *Venation.*—Smooth midrib, veins sunken.
2. Leaf attachment: Petiolate.
3. Leaf arrangement: Alternate, horizontal to slightly vertical.
4. Petiole: One-half to three-fourths leaf length, erect, round, flattened on upper surface.
5. Stem: Very short, appears to be non-existant, leaves appear to arise from crown.
6. Overall appearance: Self-heading, true rosette, free standing.

SIZE CHARACTERISTICS OF TYPICAL MATURE COMMERCIAL PLANT

1. Leaf:
   a. *Width-widest point.*—7".
   b. *Width-1" from top.*—2½"-3".
   c. *Length.*—12"-14".
   d. *Thickness.*—0.020.
2. Petioles:
   a. *Length.*—10".
   b. *Diameter (center).*—¼".
   c. *Internode spacing.*—¼"-½".
   d. *Stem diameter.*—1".

COLOR CHARACTERISTICS

1. Leaf (mature):
   a. *Top.*—21-15 grayish olive green.
   b. *Bottom.*—26-14 olive brown.
2. Leaf (immature):
   a. *Top.*—30-15 moderate reddish brown.
   b. *Bottom.*—38-15 dark red.
3. Leaf veination:
   a. *Midrib.*—24-15 dark olive.
   b. *Veins.*—23-15 dark olive.
4. Stem: 34-15 reddish brown.
5. Petiole: 34-16 reddish brown.

I claim:

1. A new and distinct variety of Philodendron plant, substantially as herein shown and described, characterized particularly as to novelty by the unique combination of self heading growth habit, distinctive hooked, lobed leaf form, the leaves with reddish brown coloration, which ultimately produce a plant having overall reddish coloration enhanced by moderate light, freedom from "shot gun" fungus problems, upright symmetrical growth without requiring staking and average height of eighteen to twenty four inches in about one year.

* * * * *